United States Patent [19]
Suzuki et al.

[11] Patent Number: 5,908,746
[45] Date of Patent: Jun. 1, 1999

[54] METHOD FOR ANALYZING BIOLOGICALLY ACTIVE SUBSTANCES

[75] Inventors: Osamu Suzuki; Naokazu Sasaki; Tatsuo Ichihara; Sanae Okada, all of Tokyo, Japan

[73] Assignee: Nisshinbo Industries, Inc., Japan

[21] Appl. No.: 08/660,295

[22] Filed: Jun. 7, 1996

[30] Foreign Application Priority Data

Jun. 9, 1995 [JP] Japan ................................ 7-143715

[51] Int. Cl.$^6$ .............................. C12Q 1/68; C12Q 1/00; C07H 21/04
[52] U.S. Cl. .................................. 435/6; 435/7.1; 435/4; 536/24.3; 935/77; 935/78
[58] Field of Search ...................... 435/4, 6, 7.1; 935/77, 935/78, 231, 25.4; 536/23.4, 22.1

[56] References Cited

U.S. PATENT DOCUMENTS

| | | | |
|---|---|---|---|
| 3,929,733 | 12/1975 | Alberino et al. | 260/77.5 R |
| 4,280,992 | 7/1981 | Sugiura et al. | 424/1 |
| 5,104,791 | 4/1992 | Abbott et al. | 435/6 |
| 5,122,600 | 6/1992 | Kawaguchi et al. | 536/27 |
| 5,514,785 | 5/1996 | Van Ness et al. | 536/22.1 |
| 5,582,970 | 12/1996 | Wallace | 435/6 |
| 5,622,826 | 4/1997 | Varma | 435/6 |

FOREIGN PATENT DOCUMENTS

| | | |
|---|---|---|
| 0 277 361 A1 | 8/1988 | European Pat. Off. . |
| 0 398 069 A2 | 11/1990 | European Pat. Off. . |
| 0 623 589 A1 | 11/1994 | European Pat. Off. . |
| 0 710 666 A1 | 5/1996 | European Pat. Off. . |
| 8-23975 | 1/1996 | Japan . |

OTHER PUBLICATIONS

Zhang et al. Nucleic Acids Research 19(14): 3929–3933 (Jul. 25, 1991).

Arrand et al. in Nucleic Acid Hybridization, Hames et al editors. IRL Press, Washington DC (1985 / pp. 17–45).

Patent Abstracts of Japan, JP 04 021637 (Soken Kagaku KK) Jan. 24, 1992). Abstract only.

Desai et al., "Polymer Bound EDC (P–EDC); A Convenient Reagent for Formation of an Amide Bond", *Tetrah. Ltrs.*, vol. 34, No. 48, pp. 7685–7688, 1993.

Rasmussen, et al., "Covalent Immobilization of DNA onto Polystyrene Microwells: The Molecules are Only Bound at the 5' End", *Analy. Biochem.*, vol. 198, pp. 138–142 (1991).

*Primary Examiner*—W. Gary Jones
*Assistant Examiner*—Debra Shoemaker
*Attorney, Agent, or Firm*—Jones & Askew

[57] ABSTRACT

A method is provided, comprising the steps of reacting a biologically active first substance immobilized on a carrier with a second substance capable of specifically binding the first substance, and detecting a non-bound part of the second substance or a bound part of the second substance indirectly bound to the carrier through binding between the first and second substances so that the first substance or the second substance in a sample is analyzed, wherein the carrier carries a compound having 2 to 100 carbodiimide groups, and the first substance is immobilized on the carrier through the carbodiimide groups so that the active substance such as protein and nucleic acid is bound to the carrier conveniently, efficiently, and tightly.

11 Claims, No Drawings

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:1:

GAATTCGAGG GTACCCGGGG ATCCTCTAGA                               30

(2) INFORMATION FOR SEQ ID NO:2:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:2:

CTAGAGGATC CCCGGGTACC CTCGAATTC                                29

(2) INFORMATION FOR SEQ ID NO:3:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:3:

AGCTAGCTAG CTAGCTAGCT AGCTAGCTAG                               30

(2) INFORMATION FOR SEQ ID NO:4:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:4:

CAAGCTTGCA TGCCTGCAGG TCGACTCTAG AGGATCCCCT                       40

(2) INFORMATION FOR SEQ ID NO:5:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:5:

CTGACTGACT GACTGACTGA CTGACTGACT GACTGACTGA                       40

-continued (2) INFORMATION FOR SEQ ID NO:6:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:6:

ACCTCCGGCT TAGGTTGGGT TATATAACTA TATGTAAAT        39

METHOD FOR ANALYZING BIOLOGICALLY ACTIVE SUBSTANCES

TECHNICAL FIELD

The present invention relates to a material for detecting biologically active substances such as nucleic acid, antibody, and antigen. The present invention also relates to a method for such detection.

BACKGROUND ART

Biologically active substances such as nucleic acid, antibody, and antigen existing in a specimen are detected and identified in certain fields such as clinical examination, food inspection, and medicolegal inspection. Several methods are used for such detection and identification depending on objective substances, including, for example, nucleic acid probe techniques and enzyme immunoassay methods.

The field, in which nucleic acid is detected, includes, for example, identification of microbial species such as pathogenic microorganisms, and DNA tests in legal medicine. Usually, in the detection of nucleic acid, a nucleic acid having a sequence complementary to a target nucleic acid is used, which is directly labeled with an enzyme or the like, or indirectly labeled through a hapten or the like. The labeled nucleic acid is hybridized with the target nucleic acid. The presence and the amount of the target nucleic acid can be confirmed by detecting a hybridized labeled portion after removing a non-hybridized part of the labeled nucleic acid or after inactivating a non-hybridized labeled portion.

The field, in which antigen, antibody or the like is detected, includes, for example, identification of microbial species such as pathogenic microorganisms in the same manner as described for the nucleic acid, as well as various clinical examinations. A competitive enzyme immunoassay method, which is an embodiment of the enzyme immunoassay method used to detect antigen and antibody, is performed as follows. An antibody or an antigen is immobilized on a surface of a solid phase such as polystyrene bead, microtiter plate, and tube. A certain amount of a specimen solution is applied to the solid phase surface, and then an antigen-enzyme complex or an antibody-enzyme complex is added. When the antibody is immobilized on the solid phase surface, the antigen in the specimen and the antigen-enzyme complex compete in a binding reaction to the antibody immobilized on the solid phase surface. When the antigen is immobilized on the solid phase surface, the antigen in the specimen and the antigen immobilized on the solid phase surface compete in a binding reaction to the antibody-enzyme complex.

After passage of a certain period of time, when the antibody is immobilized, the antigen and the antigen-enzyme complex, which do not bind to the immobilized antibody, are washed and removed. When the antigen is immobilized, unreacted parts of the antigen in the specimen and the antibody-enzyme complex, and a bound product between the antigen i n the specimen and the antibody-enzyme complex are washed and removed. The washing in this procedure is usually performed by repeating a washing operation several times to ten times. The washing operation comprises filling a solid phase section with a washing solution, discarding the washing solution, filling the solid phase section with a fresh washing solution again, and discarding the washing solution again. This operation is generally called "B/F separation" which is an essential operation in the inspection based on the principle of the enzyme immunoassay method.

In the final step, a coloring substrate solution for the enzyme used to label the antigen or the antibody is added to the solid phase section, and then a color is developed by the remaining enzyme. Generally, the enzyme used in this procedure is, for example, peroxidase, β-galactosidase, and alkaline phosphatase. A substrate appropriate for each enzyme is used as the substrate for color development. If the antigen as the target exists in a large amount in the specimen solution, the amount of the remaining antigen-enzyme complex or the remaining antibody-enzyme complex is decreased, resulting in a weak intensity of color development. The intensity of color development is generally measured by using a calorimeter.

In a sandwich enzyme immunoassay method as another embodiment of the enzyme immunoassay method, an antibody is immobilized on a solid phase surface, and a specimen solution is applied to the solid phase surface. After passage of a certain period of time, a part of an antigen which does not bind to the antibody on the solid phase surface is washed and removed. After that, a certain amount of an antibody-enzyme complex is added. After passage of a certain period of time, a part of the antibody-enzyme complex which does not bind to the antigen on the solid phase surface is washed and removed, and then a coloring substrate is applied to the solid phase surface to develop a color. The concentration of the antigen in the specimen can be quantitatively determined by measuring the intensity of the color development.

It is extremely important to immobilize antibody, antigen, enzyme, nucleic acid, or the like on the solid phase surface such as tube, microtiter plate, membrane filter, and beads in the conventional methods such as the nucleic acid detection method, the competitive enzyme immunoassay method, and the sandwich enzyme immunoassay method described above. Accordingly, various methods for immobilizing biologically active substances have been published. For example, known methods for protein include:

(1) a method for chemically binding a protein to a base material by using a cross-linking agent or a condensation agent, such as a diazo method, a peptide method, an alkylation method, a base material-binding method by using a cross-linking agent, and a base material-binding method based on Ugi reaction (see "Immobilized Enzyme", ed. by Ichiro Chibata, Kodansha Scientific (1986), pp. 9–41);

(2) a method for immobilization to a base material by using ionic bond (see "Immobilized Enzyme", pp. 41–43); and (3) a method for immobilization to a base material by using physical adsorption (see "Immobilized Enzyme", pp. 43–45).

Known methods for nucleic acid include, for example:

(1) a method for chemically binding nucleic acid which is provided with an introduced modified group, as exemplified by immobilization through a disulfide bond between nucleic acid having a thiol group at its 5'-terminal and a bead-shaped base material involving a thiol group (see P. J. R. Day, P. S. Flora, J. E. Fox, M. R. Walker, *Biochm. J.*, 278, 735–740 (1991)) (other methods belonging to this category are described in, for example, Soren R. R., Mette R. L., Svend E. R., *Anal. Biochm.*, 198, 138–142 (1991); Jonathan N. K., Joseph L. W., Joseph P. D., Rachel E. M., Mary C., Eugene L. B., *Nucleic Acids Res.*, 15, 2891–2909 (1987); Allan J. M., Jeffrey R. B., Terence W. P., *Biochem. J.*, 191, 855–858 (1980); J. A. Running, M. S. Urdea, *BioTechniques*, 8, 276–279 (1990)); and (2) a method for immobilizing nucleic acid by using physical adsorption such as immobilization by adsorption onto a nitrocellulose or nylon membrane by means of UV irradiation or heat treatment (J. Sambrok, E. F. Fritsch and T. Maniatis, *Molecular Cloning*, Cold Spring Harbor Laboratory Press, Second Edition, pages 2.109–2.113 and pages 9.34–9.46), and immobilization by physical adsorption onto a microplate (G. C. N. Parry and A. D. B. Malcolm, *Biochem. Soc. Trans.*, 17, 230–231 (1989).

However, it has been pointed out that the conventional methods as described above have drawbacks. For example, the method based on chemical bond requires special reagents including, for example, toxic substances such as azide, isocyanate, and $NaBH_3CN$. Further, when immobilization is performed by using peptide bond, for example, it is necessary to introduce an amino group into any one of an active substance and a base material, and it is necessary to introduce a carboxyl group into the other. Moreover, it is necessary to provide a step of mutually treating both of the introduced functional groups with a condensation reagent to achieve immobilization. Accordingly, it is inevitable to suffer complicated operations.

In the case of the method based on chemical bond, for example, amino groups must be present in both of the base material and the active substance in order to use glutaraldehyde as a cross-linking agent. Accordingly, it is necessary to select the base material because the base material itself must have the functional group. As a result, it becomes difficult to select the base material suitable for immobilization. In addition, for example, the method base on a chemical reaction is difficult to be used for those having only functional groups with poor reactivity (for example, terminal phosphate group, and terminal hydroxyl group) such as natural DNA and DNA having no modified group. Thus the method based on chemical bond has a drawback that immobilization cannot be achieved when the active substance has no active functional group.

On the other hand, the physical adsorption has the following drawback. Namely, the amount of immobilization is affected by adsorption performance of the base material, and the adsorbed active substance is liable to desorb. When the active substance is a low-molecular weight compound (oligomer), it is scarcely adsorbed because it has weak interaction with the base material.

As described above, many problems remain in the immobilization which is important to detect active substances such as protein and nucleic acid.

DISCLOSURE OF THE INVENTION

The present invention has been made in order to provide a method for detecting biologically active compounds by using a material comprising a high-molecular compound having carbodiimide groups capable of immobilizing biologically active substances conveniently, efficiently, and tightly.

In order to achieve the object described above, the present invention adopts a combination of characteristic materials for immobilizing biologically active substances, comprising a base material and a high-molecular compound having carbodiimide groups carried on the base material. In order to achieve the object described above, the present invention adopts a characteristic method for immobilizing biologically active substances, comprising the step of contacting materials for immobilization including a base material and a high-molecular compound having carbodiimide groups carried on the base material with a biologically active substance having reactivity with the carbodiimide groups.

Low-molecular weight carbodiimide derivatives such as dicyclohexylcarbodiimide and di-p-toluoylcarbodiimide have been hitherto widely used as a dehydrating condensation agent in synthesis of ester and peptide. The carbodiimide derivative readily forms an addition product together with carboxylic acid as illustrated in the following reaction formula (general formula (I)). The addition product condenses with, for example, alcohol, amine, or carboxylic acid while releasing a urea derivative to form corresponding ester, amide, or acid anhydride respectively (general formulae (II)). Accordingly, it is thought of that such a low-molecular weight carbodiimide derivative may have a possibility to be used to immobilize active substances.

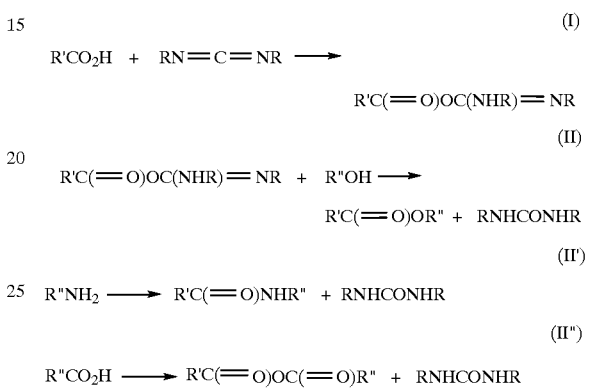

However, the low-molecular weight carbodiimide derivatives as described above are such reagents that have been developed as condensation agents, to which solubility in solvent is added. Accordingly, it has been revealed that they are liable to desorb and they cannot be practically used for the purpose of use to apply them to the base material and allow them to be carried on the surface of the base material. Thus the present inventors have paid attention to a high-molecular carbodiimide compound containing carbodiimide groups in its molecule, and the present inventors have continued diligent studies. As a result, it has been found out that such a carbodiimide compound not only has reactivity with active substances, but also has good adhesive property with respect to various types of base materials, and hence it can be applied to detection of a wide variety of biologically important compounds by utilizing immobilized substances. Thus the present invention has been completed.

Namely, the present invention lies in a method for analyzing biologically active substances, comprising the steps of:

reacting a biologically active first substance immobilized on a carrier with a second substance capable of specifically binding the first substance; and detecting a non-bound part of the second substance or a bound part of the second substance indirectly bound to the carrier through binding between the first and second substances so that the first substance or the second substance in a sample is analyzed;

wherein the carrier comprises a compound having 2 to 100 carbodiimide groups, and the first substance is immobilized on the carrier through the carbodiimide groups.

The present invention will be explained in detail below.

<1> Carrier

The carrier used in the present invention is provided for immobilizing the biologically active substance on a solid phase, which comprises the high-molecular compound having carbodiimide groups. Usually, the carrier is provided by allowing a base material to carry the high-molecular compound having carbodiimide groups.

(1) Base material

The base material used in the present invention serves as a support for immobilizing the biologically active substance. Basically, the base material is insoluble in water or solvent or both of them, and it is a solid or gel at normal temperature or within a temperature range in the vicinity thereof (0 to 100° C.), including, for example, plastics, inorganic high-molecular compounds, metals, natural high-molecular compounds, and ceramics.

The plastics specifically include, for example, polyethylene, polystyrene, polycarbonate, polypropylene, polyamide, phenol resin, epoxy resin, polycarbodiimide resin, polyvinyl chloride, polyfluorovinylidene, polyfluoroethylene, polyimide, and acrylic resin.

The inorganic high-molecular weight compounds specifically include, for example, glass, crystal, carbon, silica gel, and graphite.

The metals specifically include metals which are solid at normal temperature, such as gold, platinum, silver, copper, iron, aluminum, magnet, paramagnet, and apatite.

The natural high-molecular compounds specifically include, for example, cellulose, cellulose derivatives, chitin, chitosan, alginic acid, and salt of alginic acid.

The ceramics specifically include, for example, alumina, silica, silicon carbide, silicon nitride, and boron carbide.

The base material described above may have a certain shape or form including, for example, films, plates, particles, molded products (beads, strips, wells or strips of multi-well plates, tubes, meshes, continuous foamed foams, membranes, paper or sheet, needle, fiber, plates, slides, and vessels for cultured cells), and latexes. Of course, the size or dimension of the base material is not specifically limited.

(2) High-molecular compound having carbodiimide groups

The high-molecular compound having carbodiimide groups used in the present invention (hereinafter simply referred to as "carbodiimide compound", if necessary) includes, for example, polycarbodiimide which can be produced in accordance with a method disclosed in Japanese Patent Laid-open No. 51-61599, a method of L. M. Alberino et al. (*J. Appl. Polym. Sci.*, 21, 190 (1990)), or a method disclosed in Japanese Patent Laid-open No. 2-292316. Namely, the polycarbodiimide includes those which can be produced from an organic polyisocyanate compound in the presence of a catalyst (for example, 3-methyl-1-phenyl-2-phospholene-1-oxide) to facilitate carbodiimide formation of isocyanate.

The organic polyisocyanate compound described above includes, for example, 4,4'-dicyclohexylmethane diisocyanate, m-tetramethylxylylene diisocyanate, 2,4-tolylene diisocyanate, 2,6-tolylene diisocyanate, mixture of 2,4-tolylene diisocyanate and 2,6-tolylene diisocyanate, crude tolylene diisocyanate, crude methylenediphenyl diisocyanate, 4,4',4"-triphenylmethylene triisocyanate, xylene diisocyanate, hexamethylene-1,6-diisocyanate, lysine diisocyanate, hydrogenated methylenediphenyl diisocyanate, m-phenyl diisocyanate, naphthylene-1,5-diisocyanate, 4,4'-biphenylene diisocyanate, 4,4'-diphenylmethane diisocyanate, 3,3'-dimethoxy-4,4'-biphenyl diisocyanate, 3,3'-dimethyldiphenylmethane-4,4'-diisocyanate, isophorone diisocyanate, and arbitrary mixtures thereof.

Polycondensation takes place by converting the isocyanate group of the polyisocyanate compounds or the mixture thereof described above into carbodiimide. In this procedure, the molecular weight (degree of polymerization) can be adjusted by adding an appropriate amount of one or more species of monoisocyanate at an appropriate stage so that the terminal of the carbodiimide compound is sealed. Alternatively, monoisocyanate may be added in an appropriate amount from the beginning of the polycondensation reaction. Such monoisocyanate includes, for example, phenyl isocyanate, (o, m, p)-tolyl isocyanate, dimethylphenyl isocyanate, n-butyl isocyanate, cyclohexyl isocyanate, and methyl isocyanate. The degree of polymerization can be also adjusted by changing the concentration of, for example, the polyisocyanate compound or the reaction time.

Another terminal-sealing agent, which may be readily thought of, may be used. Namely, the terminal-sealing agent may be derived from an isocyanate-terminated compound which can be conveniently produced by using a reaction between about 1 mol of a compound having an alkyl group having terminal functional groups such as —OH, —NH$_2$, —COOH, —SH, and —NH and 2 mol of aromatic diisocyanate.

The catalyst to facilitate carbodiimide formation of the organic isocyanate may be exemplified by various compounds. However, preferred are 1-phenyl-2-phospholene-1-oxide, 3-methyl-1-phenyl-2-phospholene-1-oxide, 1-ethyl-2-phospholene-1-oxide, and 3-phospholene isomers thereof from the viewpoint of yield and the like.

The polycarbodiimide is produced with no solvent or in an unreactive organic solvent. In the present invention, for example, one species of varnishy or solid (powder) polycarbodiimide or a mixture thereof thus produced can be used. The polycarbodiimide may be partially cross-linked in order to increase the binding ability with respect to the base material.

Other carbodiimide compounds, which may be used in the present invention, include carbodiimide compounds of a type having a hydrophilic property provided by adding a polyoxyethylene chain in their molecular structures, as described in, for example, Japanese Patent Laid-open Nos. 63-172718 and 63-264128.

Even in the case of any type, the carbodiimide high-molecular compound used in the present invention preferably has, in its molecule, carbodiimide groups of a number of not less than 2 and not more than 100. If the number of carbodiimide groups of the carbodiimide high-molecular compound is less than 2, namely 1, the compound is deficient in ability to immobilize the biologically active substance. On the contrary, if the number of carbodiimide groups is not less than 101, no problem arises in relation to the performance. However, in some cases, such a compound has too high viscosity, or it cannot be prepared in a solution, sometimes resulting in deterioration of handling properties when such a compound is carried on the base material.

The carbodiimide high-molecular compound used in the present invention preferably has a molecular weight in a range of not less than 1,000 and not more than 100,000.

It is noted that some of the polycarbodiimides, produced from the organic polyisocyanate compound in the presence of the catalyst to facilitate carbodiimide formation of isocyanate, have a molecular weight of less than 1,000. However, the molecular weight of such polycarbodiimide may be adjusted to be within the range described above by introducing, for example, polyalkylene, polyoxyalkylene, polyurethane, or polyamine into both ends of the polycarbodiimide through urea bond or urethane bond.

As explained above, the carbodiimide group of the carbodiimide high-molecular compound has high reactivity, and it reacts with almost all active hydrogen groups possessed by alcohol, amine, thiol, phenol, and carboxylic acid. Reactions other than the reaction of the carbodiimide derivative with carboxylic acid described above are as follows. For example, the reaction proceeds with alcohol as shown in the following formula (III), and the reaction proceeds with amino group as shown in the following formula (IV) (see Frederick Kurzer, K. Douraghi-Zadeh, *Chemical Reviews*, 67, 117–135 (1967); and Andrew Williams, Ibrahim T. Ibrahim, *Chemical Reviews*, 81, 599–606 (1981)). Accordingly, the present invention utilizes such reactivity to immobilize the active substance onto the base material.

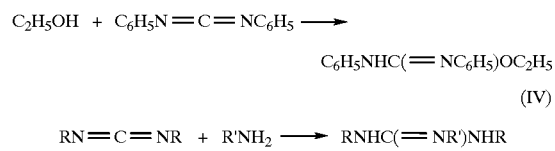

(3) Preparation of carrier

The carrier for immobilizing the biologically active substance on the solid phase used in the present invention comprises the base material and the carbodiimide compound carried on the base material. The high adhesive property of the carbodiimide compound with respect to the base material is utilized to allow the base material to carry the carbodiimide compound thereon. The term "carry" herein means the fact that the carbodiimide compound is not disengaged or desorbed from the base material in water or solvent.

Optionally, the carbodiimide compound may be carried on an entire surface of the base material, or it may be carried on a part of the base material. A representative carried form is a coating.

It is possible to adopt, as the method for carrying the carbodiimide compound on the base material, known means such as spraying, immersion, brushing, stamping, vapor deposition, coating with a film coater.

The carrier for immobilizing the active substance on the solid phase of the present invention thus obtained is capable of immobilizing various active substances by utilizing the reactivity of the carbodiimide compound.

<2> Biologically active substance

The biologically active first substance to be immobilized on the carrier includes, for example, proteins, peptides, other antibody-binding substances, and biopolymers such as nucleic acid.

Specifically, the protein and the peptide include, for example, proteinaceous hormones or peptide hormones such as insulin, ACTH (adrenocorticotropic hormone), and oxytocin; enzymes or precursors thereof such as choline esterase, amylase, and pepsin; proteinaceous antigens such as HBs antigen and HIV antigen; and antibody-binding proteins such as protein A. The antibody-binding substance includes, for example, low-molecular weight hapten. The nucleic acid includes, for example, natural or synthetic DNA (including oligonucleotide) and RNA (including oligonucleotide).

Specifically, for example, the following compounds can be referred to. Physiologically active substances having anti-microbial activity are referred to and exemplified by penicillin, ampicillin, cephalosporin, kanamycin, streptomycin, fradiomycin, destomycin, kasugamycin, tylosin, erythromycin, oleandomycin, spiramycin, lincomycin, colistin, bacitracin, salinomycin, monensin, lasalocid, tetracycline and its related substances, chloramphenicol, and virginiamycin. Synthetic antimicrobial agents are referred to and exemplified by sulfa drug, oxolinic acid, piromidic acid, furazolidone, and difurazone. Natural toxins are generally referred to and exemplified by aflatoxin, T2 toxin, zearalenone, deoxynivalenol, patulin, fumonisin, HT-2, ochratoxin, tetrodotoxin, okadaic acid, saxitoxin, gonyautoxin, and botulinum toxin. Synthetic chemicals are referred to and exemplified by general agricultural chemicals such as dioxin, 2,4-D, benomyl, aldicarb, carbofuran, methomyl, DDVP, malathon, paraquat, diazinon, fenitrothion, endrin, aldrin, and heptachlor. Biochemicals are generally referred to and exemplified by hemoglobin, α-fetoprotein, immunoglobulin, albumin, antithrombin, thrombin, plasminogen, ferritin, thyroglobulin, gelatin, cholesterol, testosterone, corticosterone, progesterone, ergosterol, estradiol, cytochrome C, adrenaline, and various vitamins.

The biologically active substance further includes antibodies capable of binding the biologically active substance such as proteins, peptides, and the like as described above. The antibody is obtained, for example, by immunizing immunizable animals including mammalians such as rat, guinea pig, rabbit, mouse, goat, sheep, horse, and bovine with the substance described above or a conjugate of the substance described above and a carrier for immunization. Alternatively, the antibody is obtained as a monoclonal antibody produced, after imminization of mouse, by hybridoma of lymphocyto of the immunized mouse and mouse myeloma cells.

On the other hand, the biologically active second substance is protein, peptide, antigenic substance, nucleic acid, or another physiologically active substance, which specifically binds to the first substance. Namely, when one of the first and second substances is protein, nucleic acid, or another physiologically active substance, the other is antibody corresponding thereto. When one of the substances is a first nucleic acid, the other is a second nucleic acid having a nucleotide sequence substantially complementary to a nucleotide sequence of the first nucleic acid. The term "substantially complementary" refers to the fact that even if one or more mismatches are present, each of nucleic acid chains is capable of hybridization through hydrogen bond to form a double strand.

It is noted that either the first substance or the second substance may be used as an object of analysis.

<3> Analysis of biologically active substance

The biologically active substance is analyzed in accordance with the method of the present invention by binding the biologically active first substance to the carrier as described above, reacting the bound first substance with the second substance, and detecting a non-bound part of the second substance or a bound part of the second substance indirectly bound to the carrier through binding between the first and second substances.

The first substance may be immobilized on the carrier by contacting the material with the active substance. The first substance and the carbodiimide high-molecular compound make covalent bond by the reaction between the carbodiimide group of the carbodiimide high-molecular compound carried on the carrier and the hydroxyl group, amino group, thiol group, carboxyl group or the like possessed by the first substance. As a result, the first substance is immobilized on the carrier.

Preferably, the first substance is contacted with the carrier in water or buffer so that the biological activity of the first substance is maintained. Preferably, the temperature during the contact is 0 to 100° C. so that the activity of the active substance is not deteriorated as well.

Preferably, in order to prevent the second substance or the like from non-specific binding to the carrier, the carrier is contacted with an excessive amount of, for example, bovine serum albumin (BSA), casein, or salmon sperm DNA after immobilizing the first substance on the carrier so that free carbodiimide groups are blocked.

As for the biologically active substance immobilized on the solid phase obtained as described above, the substance is immobilized on the carrier extremely tightly, which is not disengaged from the carrier even when it undergoes a washing procedure (for example, washing procedure by using a surfactant) widely used in the field of immunoassay. Thus this method has a field of immunological application of a carrier on which an antibody or an antigen is immobilized, and a field of application of a nucleic acid-immobilized carrier as a diagnostic agent.

After the first substance immobilized on the carrier is reacted with the second substance, the second substance bound to the carrier is detected in the same manner as performed in ordinary methods for solid phase immunoassay and nucleic acid hybridization. For example, when the first substance is a measurement object, then the second substance labeled with a label substance is reacted with the immobilized first substance, and the label substance immobilized on the carrier is detected or quantitatively measured. Thus a bound part of the second substance can be detected or quantitatively measured. As a result, the first substance can be detected or quantitatively measured. Instead of the part of second substance bound to the first substance, a non-bound part of the second substance may be detected or quantitatively measured.

When the second substance is a measurement object, a certain amount of the second substance labeled with a label substance is further added to the reaction system during the reaction between the first and second substances. Thus the amount of the second substance in a sample can be indirectly measured on the basis of a binding amount of the labeled second substance bound to the first substance (inhibition method).

Alternatively, the second substance bound to the carrier can be also detected by making a reaction of a third substance which is capable of specifically binding the second substance. For example, when the second substance is an antigen, and the first substance is a polyclonal antibody or a monoclonal antibody (primary antibody) against the antigen, then a carrier-antibody-antigen complex is reacted with a polyclonal antibody or another monoclonal antibody concerning an epitope different from that for the monoclonal antibody described above (secondary antibody) so that a carrier-antibody-antigen-antibody complex is formed to detect the third substance in the complex. Thus the second substance can be detected (sandwich method). In this procedure, when the third substance is labeled, its label may be detected. Even when the third substance is not labeled, an additional substance which binds to the third substance may be used provided that the additional substance has been labeled. For example, in the aforementioned case, the primary antibody is prepared in an animal different from that used for preparation of the secondary antibody, and the antibody against immunoglobulin of the animal used for preparation of the secondary antibody is used as the third substance. In the case of detection of nucleic acid, the procedure is designed in the same manner as described above. Namely, a first nucleic acid is immobilized on the carrier, and a second nucleic acid having specificity to the first nucleic acid is bound to the first nucleic acid. A third nucleic acid, which has specificity to the second nucleic acid but does not have specificity to the first nucleic acid, is bound to an obtained product. Thus the second nucleic acid can be quantitatively measured on the basis of the amount of the third nucleic acid bound to the carrier.

Alternatively, the second substance can be also detected by using an emulsive carrier in accordance with a general agglutination method.

The label substance includes, for example, radioactive substances, fluorescent substances, enzymes, dyes, chemical luminescent substances, and digoxigenin. When the labeling is made by using a radioactive substance, a fluorescent substance, or a dye, the label can be directly detected by measurement by using a scintillation counter, exposure of a film, or observation with the naked eye. When an enzyme is used, a substrate dye, which develops color as a result of an enzymatic reaction, may be used to detect its color development. Such an enzyme may include those generally used, including, for example, peroxidase, $\beta$-D-galactosidase, alkaline phosphatase, and lysozyme.

It may be not necessarily indispensable that the label substance itself is detectable. For example, when biotin is used as the label substance, an enzyme conjugated with avidin or streptoavidin which specifically binds to biotin is used. Thus biotin can be indirectly detected.

Unreacted substances are removed, namely B/F separation is performed after the reaction of the first and second substances and optionally the third substance or other substances. This procedure may be performed in the same manner as performed in ordinary methods of solid phase immunoassay and hybridization. Namely, when the carrier has a shape of a vessel, an operation comprising filling the carrier with a washing solution and discarding the washing solution is repeated several times. When the carrier has a form of particles, an operation comprising suspending the carrier in a washing solution may be repeated.

According to the present invention, the immobilization on the carrier, which is important to detect active substances such as protein and nucleic acid, can be performed conveniently, efficiently, and tightly.

Best Mode for Carrying Out the Invention

The present invention will be more specifically explained below with reference to Examples.

PRODUCTION EXAMPLE 1

Production of Carbodiimide Compound Solution
(1)

4,4'-Dicyclohexylmethane diisocyanate (117.9 g) and cyclohexyl isocyanate (12.5 g) were reacted at 180° C. for 4 days under a nitrogen atmosphere together with a catalyst for carbodiimide formation (3-methyl-1-phenyl-2-phospholene-1-oxide, 1.3 g) to obtain a carbodiimide compound (degree of polymerization: 10, number-average molecular weight: 2,400) which was powder at room temperature. The obtained compound (10 g) was dispensed, and it was dissolved in methanol (100 ml) to obtain a carbodiimide compound solution 1.

PRODUCTION EXAMPLE 2

Production of Carbodiimide Compound Solution
(2)

Isophorone diisocyanate (19.9 g) and n-butyl isocyanate (2.0 g) were reacted at 180° C. for 3 days under a nitrogen atmosphere together with a catalyst for carbodiimide formation (3-methyl-1-phenyl-2-phospholene-1-oxide, 0.2 g) to obtain a carbodiimide compound (degree of polymerization: 10, number-average molecular weight: 1,900) which was powder at room temperature. The obtained compound (10 g) was dispensed, and it was dissolved in dichloromethane (100 ml) to obtain a carbodiimide compound solution 2.

PRODUCTION EXAMPLE 3

Production of Carbodiimide Compound Solution (3)

A mixture of 2,4-tolylene diisocyanate/2,6-tolylene diisocyanate (mixing ratio=80:20, 78.4 g) and phenyl isocyanate (11.9 g) were reacted in tetrachloroethylene (615 g) at 75° C. for 24 hours under a nitrogen atmosphere together with a catalyst for carbodiimide formation (3-methyl-1-phenyl-2-phospholene-1-oxide, 0.9 g) to obtain a carbodiimide compound solution 3 (degree of polymerization: 10, number-average molecular weight: 1,500).

PRODUCTION EXAMPLE 4

Production of Carbodiimide Compound Solution (4)

4,4-Diphenylmethane diisocyanate (112.6 g) and phenyl isocyanate (11.9 g) were reacted in tetrahydrofuran (922.7 g) at 75° C. for 16 hours under a nitrogen atmosphere together with a catalyst for carbodiimide formation (3-methyl-1-phenyl-2-phospholene-1-oxide, 1.2 g) to obtain a carbodiimide compound solution 4 (degree of polymerization: 10, number-average molecular weight: 2,300).

PRODUCTION EXAMPLE 5

Production of Carbodiimide Compound Solution (5)

m-Tetramethylxylylene diisocyanate (700 g) and a catalyst for carbodiimide formation (3-methyl-1-phenyl-2-phospholene-1-oxide, 14 g) were reacted at 180° C. for 12 hours under a nitrogen atmosphere to obtain isocyanate-terminated tetramethylxylylene carbodiimide (degree of polymerization: 3). After that, the obtained carbodiimide (74.6 g) and poly(oxyethylene) monomethyl ether (degree of polymerization: 6, 63.6 g) were reacted at 100° C. for 48 hours. An obtained product (10 g) was dispensed, and distilled water (90 g) was gradually added thereto at 50° C. to obtain a carbodiimide compound solution 5 (number-average molecular weight: 1,400).

PRODUCTION EXAMPLE 6

Production of Carbodiimide Compound Solution (6)

4,4'-Diphenylmethane diisocyanate (162 g) was reacted in tetrahydrofuran (886 g) under reflux for 7 hours under a nitrogen atmosphere together with a catalyst for carbodiimide formation (3-methyl-1-phenyl-2-phospholene-1-oxide, 0.33 g) to obtain a carbodiimide compound solution 6 (degree of polymerization: 60, number-average molecular weight: 13,000, polymer concentration: 15% by weight).

PRODUCTION EXAMPLE 7

Production of Carbodiimide Compound Solution (7)

m-Tetramethylxylylene diisocyanate (700 g) and a catalyst for carbodiimide formation (3-methyl-1-phenyl-2-phospholene-1-oxide, 14 g) were reacted at 180° C. for 18 hours under a nitrogen atmosphere to obtain isocyanate-terminated tetramethylxylylene carbodiimide (degree of polymerization: 4). After that, the obtained carbodiimide (50.2 g) and 2-dimethylaminoethanol (8.9 g) were reacted at 80° C. for 24 hours, and then methyl p-toluenesulfonate (18.6 g) was added thereto to perform a reaction for 1 hour. Distilled water (699.3 g) was gradually added thereto to obtain a carbodiimide compound solution 7 (number-average molecular weight: 1,600, polymer concentration: 10% by weight).

PRODUCTION EXAMPLE 8

Production of Carbodiimide Compound Solution (8)

Isophorone diisocyanate (20 g) and a catalyst for carbodiimide formation (3-methyl-1-phenyl-2-phospholene-1-oxide, 0.2 g) were reacted at 180° C. for 18 hours under a nitrogen atmosphere to obtain isocyanate-terminated isophorone carbodiimide (degree of polymerization: 4). After that, the obtained carbodiimide (7.56 g) and 3-dimethylaminopropylamine (2.04 g) were reacted at 80° C. for 1 hour, and then methyl p-toluenesulfonate (3.72 g) was added thereto to perform a reaction for 1 hour. Distilled water (120 g) was gradually added thereto to obtain a carbodiimide compound solution 8 (number-average molecular weight: 1,400, polymer concentration: 10% by weight).

PRODUCTION EXAMPLE 9

Production of Carbodiimide Compound Solution (9)

4,4'-Dicyclohexylmethane diisocyanate (117.9 g) and a catalyst for carbodiimide formation (3-methyl-1-phenyl-2-phospholene-1-oxide, 1.2 g) were reacted at 180° C. for 8 hours under a nitrogen atmosphere to obtain isocyanate-terminated dicyclohexyl carbodiimide (average degree of polymerization: 2.4). After that, the obtained carbodiimide (7.85 g) and poly(oxyethylene) monomethyl ether (degree of polymerization: about 6, 5.92 g) were reacted at 100° C. for 48 hours. Distilled water (124 g) was gradually added thereto to obtain a carbodiimide compound solution 9 (number-average molecular weight: 1,300, polymer concentration: 10% by weight).

PRODUCTION EXAMPLE 10

Production of Carbodiimide Compound Solution (10)

4,4'-Dicyclohexylmethane diisocyanate (15 g) and a catalyst for carbodiimide formation (3-methyl-1-phenyl-2-phospholene-1-oxide, 0.1 g) were reacted in tetrahydrofuran (145 g) at 75° C. for 8 hours under a nitrogen atmosphere to obtain isocyanate-terminated diphenylmethane carbodiimide (degree of polymerization: 5). After that, poly (oxyethylene) monomethyl ether (degree of polymerization: 10, 9.44 g) was added to the obtained carbodiimide solution to perform a reaction at 75° C. for 48 hours to obtain a carbodiimide compound solution 10 (number-average molecular weight: 2,100, polymer concentration: 10% by weight).

PRODUCTION EXAMPLE 11

Production of Carbodiimide Compound Solution (11)

A mixture of 2,4-tolylene diisocyanate/2,6-tolylene diisocyanate (mixing ratio=80:20, 13.9 g) and a catalyst for carbodiimide formation (3-methyl-1-phenyl-2-phospholene-1-oxide, 0.1 g) were reacted in tetrahydrofuran (150 g) at 75° C. for 8 hours under a nitrogen atmosphere to obtain isocyanate-terminated tolylene carbodiimide (degree of polymerization: 4). After that, sodium hydroxypropanesulfonate (1.62 g) was added to the obtained carbodiimide solution to perform a reaction at 75° C. for 24 hours to obtain a carbodiimide compound solution 11 (number-average molecular weight: 1,000, polymer concentration: 10% by weight).

PRODUCTION EXAMPLE 12

Production of Carbodiimide Compound Solution (12)

4,4-Diphenylmethane diisocyanate (24 g) and polyethylene glycol (number-average molecular weight: 400, 20 g) were added to tetrahydrofuran (440 g) to make a reaction. After that, a catalyst for carbodiimide formation (3-methyl-1-phenyl-2-phospholene-1-oxide, 0.2 g) was reacted at 75° C. for 48 hours under a nitrogen atmosphere to obtain a carbodiimide compound solution 12 (number-average molecular weight: 5,300, polymer concentration: 10% by weight).

PRODUCTION EXAMPLE 13

Production of Carbodiimide Compound Solution (13)

4,4-Dicyclohexylmethane diisocyanate (52.4 g) and 1,4-diaminobutane (8.8 g) were added to tetrahydrofuran (620 g) to make a reaction. After that, a catalyst for carbodiimide formation (3-methyl-1-phenyl-2-phospholene-1-oxide, 0.5 g) was reacted at 75° C. for 48 hours under a nitrogen atmosphere to obtain a carbodiimide compound solution 13 (number-average molecular weight: 3,700, polymer concentration: 10% by weight).

EXAMPLE 1

Detection of DNA Immobilized on Carbo-Coated Microplate by Using Labeled DNA (1) Immobilization of DNA oligomer on microplate A capture DNA oligomer (SEQ ID NO: 1) and a biotinylated probe DNA oligomer (SEQ ID NO: 2) were synthesized by using a DNA synthesizer (produced by Millipore, Cyclone Plus DNA/RNA synthesizer). Biotin was introduced into 5'-terminal of the probe by using biotin phosphoamidite (produced by Millipore) during synthesis of the DNA oligomer.

An aliquot (0.1 ml) of the carbodiimide compound solution 1 was dispensed and poured into each of wells of a 96-well microplate made of polystyrene, which was incubated at 60° C. for 1 hour. After removal of the solution, each of the wells was washed well with ethanol. After drying at 60° C. for 30 minutes, an aqueous solution of the capture 30 mer (10 pmol/100 µl, 100 µl) was added to each of the wells, and the plate was sealed. Immobilization was performed for 1 hour in an incubator at 37° C.

On the other hand, an oligonucleotide (SEQ ID NO: 3) exhibiting no complementarity to the probe at all was prepared as a control and immobilized in the same manner as described above.

(2) Detection of capture oligonucleotide by hybridization

A prehybridization solution (100 µl/well) was added to the plate on which the capture oligonucleotide (SEQ ID NO: 1) or the control DNA oligomer had been immobilized. The plate was sealed, followed by being left for 2 hours in an incubator at 42° C. The prehybridization solution had a composition comprising 5x SSC (0.75M NaCl, 0.075M sodium citrate), 5x Denhardt's solution (0.02% Ficoll, 0.02% BSA fraction V, 0.02% polyvinylpyrrolidone), 25 mM sodium phosphate (pH 6.6), 50% formamide, and 0.5 mg/ml denatured salmon sperm DNA.

The solution in each of the wells was sucked and removed by using a dispenser. A hybridization solution (100 µl/well), to which the probe had been added, was added to the well, and the plate was sealed. A reaction was made for 15 hours in an incubator at 42° C. The hybridization solution had a composition comprising 5x SSC, 1x Denhardt's solution, 25 mM sodium phosphate (pH 6.6), 45% formamide, 0.2 mg/ml denatured salmon sperm DNA, and 10% dextran sulfate.

The probe was treated at 70° C. for 5 minutes, quickly cooled with ice for 5 minutes, and added to the hybridization solution so that it was 1, 10, or 100 pmol/well.

After the hybridization, the solution in the wall was sucked and removed, and 1x SSC (300 µl/well) was added, followed by being left at room temperature for 5 minutes. This operation was performed two more times to remove the probe having been non-specifically adsorbed.

(3) Detection

SSC in the well was sucked and removed, and buffer A (0.2M sodium chloride, 0.1M Tris-HCl (pH 7.5), 0.05% Triton X-100) containing 3% BSA was added to the well (300 µl/well) to perform blocking at room temperature for 30 minutes. The solution in the well was sucked and removed, and a solution of streptoavidin-alkaline phosphatase conjugate (produced by Gibco BRL, prepared by diluting a stock solution 5,000-fold with buffer A) was added to the well (100 µl/well) to make a reaction at room temperature for 30 minutes. The conjugate solution was sucked and removed, and buffer A was added to the well (300 µl/well), followed by being left at room temperature for 5 minutes. This operation was performed two more times to remove a part of the conjugate not bound to biotin. A solution of pNpp was added to the well (100 µl/well) to make a reaction at 30° C. for 30 minutes. The pNpp solution had a composition comprising 50 mM sodium tetraborate (pH 10.0), 5 mM magnesium chloride, and 5 mM disodium p-nitrophenylphosphate.

After the reaction, the enzyme reaction was stopped by adding an aqueous solution of 0.1N sodium hydroxide. Absorbance at 405 nm of each well was measured by using a microplate reader. As a result of the measurement, the plate on which the oligomer having no complementarity (SEQ ID NO: 3) had been immobilized had an absorbance equal to that of background, while the plate on which the capture had been immobilized provided an absorbance value exhibiting a significant difference from the background. The result is shown in Table 1.

TABLE 1

| Capture DNA | Absorbance value ($A_{405}$) |
|---|---|
| SEQ ID NO: 1 | 1.54 |
| SEQ ID NO: 3 | 0.05 |
| (background: 0.05) | |

EXAMPLE 2

Detection of M13 DNA Immobilized on Carbo-Coated Polystyrene Beads by Using Labeled M13 DNA (1) Immobilization of capture DNA on beads Polystyrene beads (5 g) were immersed in the carbodiimide compound solution 2 (100 ml) for 30 minutes, and then they were dried at 60° C. for 3 hours to obtain carbodiimide-coated beads.

The carbodiimide-coated beads (1 g) were suspended in sterilized distilled water (10 ml). Thermally denatured M13 RF DNA or pBR322 DNA was added to the suspension so that a concentration of 100 ng/ml was obtained. Immobilization was performed at 37° C. for 2 hours with shaking. The beads were washed with 500 ml of distilled water by using a filter, and they were dried in air.

(2) Hybridization

The air-dried beads (100 mg) were weighed and transferred into a disposable tube having a volume of 1.5 ml, to which the prehybridization solution (1 ml) prepared in Example 1 was added, followed by being left at 42° C. for 2 hours. The beads were separated by a centrifugation operation, to which the hybridization solution (1 ml) prepared in Example 1 was added, and the beads were suspended well. The same operation was performed two more times. The hybridization solution (1 ml) was added, and the beads were suspended well. M13 ssDNA, which had been biotin-labeled by using photobiotin (produced by VECTOR), was thermally denatured and then added so that a concentration of 1 µg/ml was obtained (pBR322, into which biotin had been introduced by means of the same labeling method, was used as a control). A reaction was performed at 42° C. for 15 hours with shaking.

The beads were separated by a centrifugation operation. A supernatant was removed, and 2× SSC (1 ml) was added. The beads were suspended well, followed by being left at room temperature for 5 minutes. This operation was repeated two more times. A supernatant was removed by a centrifugation operation, and 0.2× SSC (1 ml) was added. The beads were suspended well, followed by being left at room temperature for 5 minutes. This operation was performed two more times. A supernatant was removed by a centrifugation operation, and 0.16× SSC (1 ml) having been previously warmed at 50° C. was added. The beads were suspended well, followed by being left at 50° C. for 10 minutes. This operation was performed one more time.

A supernatant was removed by a centrifugation operation, and buffer A (1 ml) containing 3% BSA prepared in Example 1 was added, followed by being left at room temperature for 30 minutes with shaking. A supernatant was removed by a centrifugation operation, and a solution of streptoavidin-alkaline phosphatase (produced by Gibco BRL, 1 ml) having been diluted 1,000-fold with buffer A was added. The beads were suspended well, followed by being left at room temperature for 30 minutes with shaking. A supernatant was removed by a centrifugation operation, and then buffer A (1 ml) was added. The beads were suspended well, followed by being left at room temperature for 5 minutes. The same operation was performed two more times.

A supernatant was removed by a centrifugation operation, borate buffer (50 mM sodium tetraborate (pH 10.0), 0.5 mM magnesium chloride, 1 ml) was added, and the beads were suspended. This operation was performed two more times. A supernatant was removed by a centrifugation operation, and the pNpp solution (400 µl) prepared in Example 1 was added. The beads were suspended well. A reaction was performed at 30° C. for 30 minutes, and then an aqueous solution of 0.1N sodium hydroxide (800 µl) was added to stop the reaction. The absorbance at 405 nm was measured by using a spectrophotometer.

As a result, no absorbance was observed in the beads on which pBR322 had been immobilized. On the contrary, a value exhibiting a significant difference from background was obtained for the beads on which M13 DNA had been immobilized. The result is shown in Table 2.

TABLE 2

| Probe DNA | Absorbance value ($A_{405}$) |
|---|---|
| M13 ssDNA | 0.96 |
| pBR322 DNA | 0.05 |
| (background: 0.05) | |

EXAMPLE 3

Detection of DNA Oligomer Immobilized on Carbo-Coated Denatured Cellulose Membrane by Using Labeled M13 DNA (1) Immobilization of DNA oligomer A denatured cellulose filter was immersed in the carbodiimide solution 3 for 10 seconds, and then it was dried at 60° C. for 30 minutes. The filter was placed on filter paper, onto which an aqueous solution of a DNA oligomer (40 mer, SEQ ID NO: 4) and an aqueous solution of a DNA oligomer (40 mer, SEQ ID NO: 5) were spotted. The DNA oligomer (40 mer, SEQ ID NO: 4) had a sequence complementary to a multiple cloning site of M13 DNA synthesized in the same manner as described in Example 1. The DNA oligomer (40 mer, SEQ ID NO: 5) had no complementarity to M13 DNA. The aqueous solutions were spotted in an amount of 1 µl respectively as 10-order diluted solutions ranging from 1 ng to 10 fg. The filter was left at 37° C. for 15 minutes to immobilize the DNA oligomers.

(2) Hybridization

The carbo-coated denatured cellulose membrane involving the oligomers immobilized thereon was introduced into a hybridization bag (produced by Bethesda Research Laboratories) to which the prehybridization solution prepared in Example 1 was added (0.08 ml/cm² membrane). The hybridization bag was sealed by using a heat sealer, followed by being left at 42° C. for 2 hours. The membrane was taken out of the hybridization bag, and it was introduced into a new hybridization bag. The hybridization solution prepared in Example 1 containing M13 RF DNA (100 ng/ml) bioin-labeled with thermally denatured photobiotin (produced by VECTOR) was added to the bag (0.03 ml/cm²). The hybridization bag was sealed by using a heat sealer, followed by being left at 42° C. for 15 hours. The membrane was taken out of the hybridization bag, and it was introduced into a tray filled with 2× SSC in an amount enough to immerse the membrane. The tray was slowly shaken at room temperature for 5 minutes. This operation was performed again. After that, the membrane was introduced into a tray filled with an enough amount of 0.2× SSC having been warmed at 40° C., which was slowly shaken at 40° C. for 5 minutes. This operation was performed two more times. The membrane was transferred to a tray filled with 2× SSC, and it was washed well.

(3) Detection

The membrane was introduced into a new hybridization bag to which buffer A containing 3% BSA was added (1 ml/cm²). The hybridization bag was sealed by using a heat sealer, followed by being left at room temperature for 30 minutes. The membrane was taken out of the hybridization bag, and it was transferred to a new hybridization bag to which a solution of streptoavidin-alkaline phosphatase conjugate (produced by Gibco BRL, diluted 1,000-fold with buffer A) was added (0.1 ml/cm$^2$). The hybridization bag was sealed by using a heat sealer, followed by being left at room temperature for 30 minutes. The membrane was taken out of the hybridization bag, and it was transferred to a tray filled with an enough amount of buffer A so that it was washed at room temperature for 5 minutes with shaking. This operation was performed two more times.

The membrane was introduced into a new hybridization bag to which a solution of a color development substrate was added (0.1 ml/cm$^2$). The hybridization bag was sealed by using a heat sealer, followed by being left at room temperature until appropriate degrees of signals were obtained. The composition of the color development substrate was as follows. Namely, a solution of BCIP (50 mg 5-bromo-4-chloro-3-indolylphosphate/900 ml dimethylformamide, 3.2 μl) and a solution of NTB (50 mg nitroblue tetrazolium/1.8 ml 70% ethanol, 6.4 μl) were added to a solution (1 ml) of 0.1M Tris-HCl buffer (pH 9.5), 0.1M NaCl, and 50 mM magnesium chloride.

After sufficient signals were obtained, the membrane was washed with 0.2M EDTA buffer (pH 8.0) to stop the color development reaction. As a result, signals were obtained only at positions at which the oligomer having complementarity with M13 DNA had been immobilized. The result is shown in Table 3.

TABLE 3

| Immobilized DNA oligomer | Signal | | | | | |
|---|---|---|---|---|---|---|
| SEQ ID NO: 4 | ++ | ++ | ++ | ++ | + | – |
| SEQ ID NO: 5 | – | – | – | – | – | – |
| amount of oligomer used | 1 ng | 100 pg | 10 pg | 1 pg | 100 fg | 10 fg |

++: clearly visible, +: visible, –: invisible.

EXAMPLE 4

Detection of DNA Oligomer Immobilized on Carbo-Coated Microplate by Using Two-Step Hybridization (1) Immobilization of DNA oligomer The capture DNA oligomer (40 mer, SEQ ID NO: 4) complementary to M13 ssDNA was immobilized in accordance with the procedure described in Example 1.

(2) Hybridization

The prehybridization solution (100 μl) was added to each well, and the plate was sealed, followed by being left at 42° C. for 2 hours. The solution in each well was sucked and removed by using a dispenser. A hybridization solution prepared as described in Example 1 containing thermally denatured M13 ssDNA (100 ng/ml) (pBR322 was added to a control system) and a biotinylated DNA oligomer (40 mer) complementary to the thermally denatured M13 ssDNA (exhibiting no complementarity to the capture oligomer immobilized on the plate, SEQ ID NO: 6) synthesized in the same manner as described in Example 1 with its 5'-terminal biotin-labeled was added to the well (1 μg/ml, 100 μl/well). The plate was sealed, followed by being left at 42° C. for 15 hours.

The solution in each well was sucked and removed. 1× SSC was added to the well (200 μl/well), followed by being left at room temperature for 5 minutes. This operation was performed two more times.

(3) Detection

Detection was performed in accordance with the same method as described in Example 1 (3). As a result, an absorbance value exhibiting a significant difference from background was obtained in the system in which M13 ssDNA was used. On the contrary, no significant difference from the background was observed in the system in which pBR322 as the control was used. The result is shown in Table 4.

TABLE 4

| DNA | Absorbance value (A$_{405}$) |
|---|---|
| M13 ssDNA | 0.54 |
| pBR322 DNA | 0.05 |
| (background: 0.05) | |

EXAMPLE 5

Detection of IgG Immobilized on Carbo-Coated Aluminum Vapor-Deposited Film by Using Labeled Anti-IgG (1) Immobilization of IgG on metal plate Aluminum was vapor-deposited with a thickness of 2,000 angstroms onto a glass substrate to obtain a vapor-deposited film. Three dots of a rabbit IgG solution (1% gelatin, 20 mM Tris-HCl buffer (pH 7.5), 0.5M NaCl) were spotted onto the vapor-deposited film coated with any of the carbodiimide compound solutions 1-4, 6, and 10-13 (0.5 ml) by using a spin coater, and onto the aluminum vapor-deposited film not coated with the carbodiimide compound solution respectively, followed by immobilization at room temperature for 10 minutes. These aluminum vapor-deposited films were washed three times for 10 minutes in each washing with a washing solution 1 (20 mM Tris-HCl buffer (pH 7.5), 0.5M NaCl, 0.05% Tween 20).

(2) Detection of rabbit IgG by means of antigen-antibody reaction (a) Blocking

Blocking was performed at 25° C. for 30 minutes in a blocking solution (3% gelatin, 20 mM Tris-HCl buffer (pH 7.5), 0.5M NaCl).

(b) Antigen-antibody reaction

Incubation was performed at 37° C. for 2 hours in a solution of alkaline phosphatase-labeled anti-rabbit goat IgG (1% gelatin, 20 mM Tris-HCl buffer (pH 7.5), 0.5M NaCl, 0.05% Tween 20). Unreacted antibody was removed by washing with the washing solution 1 three times for 10 minutes in each washing, followed by replacement with a washing solution 2 (20 mM Tris-HCl buffer (pH 7.5), 0.5M NaCl).

(c) Color development operation

A solution of BCIP (50 mg 5-bromo-4-chloro-3-indolylphosphate, 900 ml dimethylformamide, 3.2 μl) was mixed with a solution of NTB (50 mg nitroblue tetrazolium, 1.8 ml 70% ethanol, 6.4 μl) to obtain a solution which was added to a buffer for substrate (0.1M Tris-HCl buffer (pH 9.5), 0.1M NaCl, 50 mM MgCl$_2$, 1 ml), followed by color development at room temperature for 3 hours. A result is shown in Table 5.

TABLE 5

| Carbodiimide solution | Result of color development |
| --- | --- |
| none | − |
| 1 | + |
| 2 | + |
| 3 | + |
| 4 | + |
| 6 | + |
| 10 | + |
| 11 | + |
| 12 | + |
| 13 | + |

+: color development, −: no color development.

EXAMPLE 6

Sandwich ELISA by Using Carbo-Coated Plate (1) Immobilization of IFNY on microplate The carbodiimide compound was coated in the same manner as described in Example 1 to prepare a 96-well microtiter plate made of polystyrene to which a solution of 1 µg/µl of anti-human interferon-γ (IFNγ) antibody (10 mM sodium phosphate buffer (pH 7.4), 150 mM NaCl) was dispensed and poured in an amount of 100 µl per one well, followed by being left at 4° C. overnight. Non-adsorbed antibody was removed by washing five times for 5 minutes in each washing with a washing solution 1 (sodium phosphate buffer (pH 7.4), 0.05% Tween 20).

(2) Blocking

A blocking solution (3% skim milk, 20 mM sodium phosphate buffer (pH 7.4), 0.5M NaCl) was dispensed and poured in an amount of 300 µl per one well to perform blocking at 25° C. for 30 minutes.

(3) Antigen-antibody reaction

Standard solutions were prepared with a buffer (1% skim milk, 10 mM sodium phosphate buffer (pH 7.4), 150 mM NaCl) so that IFNγ was 400 pg, 200 pg, 100 pg, 50 pg, 25 pg, and 12.5 pg, which were added in an amount of 100 µl respectively to the microtiter plate on which the anti-human IFNγ antibody had been immobilized as described in the item (1). The plate was sealed, and then it was incubated at 37° C. for 2 hours. Unreacted antigen was removed by washing five times for 5 minutes in each washing with the washing solution 1.

Next, a solution of alkaline phosphatase-labeled anti-IFNγ antibody (1% skim milk, 10 mM sodium phosphate buffer (pH 7.4), 150 mM NaCl) was added in an amount of 100 µl per one well. The plate was sealed, followed by incubation at 37° C. for 2 hours. Unreacted antibody was removed by washing five times for 5 minutes in each washing with the washing solution 1.

(4) Color development operation

A pNpp solution was prepared in the same manner as described in Example 1, which was added in an amount of 100 µl per one well. A reaction was performed at 30° C. for 25 minutes. After that, the color development was stopped by adding 100 µl of 0.1N NaOH to each well. The density of generated color was measured by using a microplate reader adjusted at an absorbance wavelength of 405 nm. A result is shown in Table 6.

TABLE 6

| IFNγ (pg/ml) | Absorbance value ($A_{405}$) |
| --- | --- |
| 1.25 | 0.115 |
| 25 | 0.192 |
| 50 | 0.385 |
| 100 | 0.731 |
| 200 | 1.462 |
| 400 | 2.731 |
| (background: 0.05) | |

EXAMPLE 7

Detection of Human Plasminogen Based on Agglutination Method by Using Emulsive Carbo-Coated Polystyrene Latex (1)

(1) Immobilization of anti-human plasminogen antibody on carbo-coated polystyrene latex A polystyrene latex comprising particles having a diameter of 0.15 µm coated with the carbodiimide compound solution 3 was prepared to have a concentration of 1% by weight with 50 mM borate buffer (pH 8.5). This solution was dispensed (1 ml), and its temperature was kept at 37° C. After that, anti-human plasminogen antibody (300 µg) was added, followed by shaking at 37° C. for 1 hour. This solution was centrifuged under a condition of 18,000 rpm at 4° C. for 1 hour to remove a supernatant.

(2) Blocking

A precipitate was suspended in a solution comprising 3% bovine serum albumin and 50 mM borate buffer (pH 8.5), followed by shaking at 37° C. for 1 hour. This solution was centrifuged under a condition of 18,000 rpm at 4° C. for 1 hour to remove a supernatant. A precipitate was suspended in 10 mM sodium phosphate buffer (pH 7.4) to give a solution having a concentration of 0.5% by weight.

(3) Measurement of change in absorbance by agglutination reaction

A human plasminogen solution (10 mg/ml, 50 µl) (3% bovine serum albumin, 10 mM sodium phosphate buffer (pH 7.4), 150 mM NaCl) and the latex solution (50 µl) with the immobilized anti-human plasminogen antibody prepared as described in the items (1) and (2) were added to 10 mM sodium phosphate buffer (pH 7.4) containing 150 mM NaCl (400 µl) and mixed. The change in absorbance of this solution at a wavelength of 660 nm was measured for 30 to 120 seconds after the start of the reaction. A test was performed as a control in the same manner as described above for 10 mg/ml of a human transferrin solution (3% bovine serum albumin, 10 mM sodium phosphate buffer (pH 7.4), 150 mM NaCl). A result is shown in Table 7.

TABLE 7

| | Amount of change in absorbance value ($A_{660}$) |
| --- | --- |
| plasminogen | 0.52 |
| transferrin | 0.005 |

EXAMPLE 8

Detection of Human Plasminogen Based on Agglutination Method by Using Emulsive Carbo-Coated Polystyrene Latex (2)

(1) Immobilization of anti-human plasminogen antibody on carbo-coated C-type Polystyrene latex A polystyrene latex containing carboxyl groups comprising particles having a diameter of 0.15 μm coated with the carbodiimide compound solution 9 was prepared to have a concentration of 1% by weight with 50 mM borate buffer (pH 8.5). This solution was dispensed (1 ml), and its temperature was kept at 37° C. After that, anti-human plasminogen antibody (300 μg) was added, followed by shaking at 37° C. for 1 hour. This solution was centrifuged under a condition of 18,000 rpm at 4° C. for 1 hour to remove a supernatant.

(2) Blocking

A precipitate was suspended in a solution comprising 3% bovine serum albumin and 50 mM borate buffer (pH 8.5), followed by shaking at 37° C. for 1 hour. This solution was centrifuged under a condition of 18,000 rpm at 4° C. for 1 hour to remove a supernatant. A precipitate was suspended in 10 mM sodium phosphate buffer (pH 7.4) to give a solution having a concentration of 0.5% by weight.

(3) Measurement of change in absorbance by agglutination reaction

A human plasminogen solution (10 mg/ml, 50 μl) (3% bovine serum albumin, 10 mM sodium phosphate buffer (pH 7.4), 150 mM NaCl) and the latex solution (50 μl) with the immobilized anti-human plasminogen antibody prepared as described in the items (1) and (2) were added to 10 mM sodium phosphate buffer (pH 7.4) containing 150 mM NaCl (400 μl) and mixed. The change in absorbance of this solution at a wavelength of 660 nm was measured for 30 to 120 seconds after the start of the reaction. A test was performed as a control in the same manner as described above for 10 mg/ml of a human transferrin solution (3% bovine serum albumin, 10 mM sodium phosphate buffer (pH 7.4), 150 mM NaCl). A result is shown in Table 8.

TABLE 8

|  | Amount of change in absorbance value ($A_{660}$) |
|---|---|
| plasminogen | 0.55 |
| transferrin | 0.005 |

EXAMPLE 9

Detection of DNA Based on Agglutination Method by Using Emulsive Carbo-Coated Carboxyl-Type Polystyrene Latex (1) Immobilization of M13 mp18ss on carbo-coated latex A polystyrene latex containing carboxyl groups comprising particles having a diameter of 0.15 μm coated with the carbodiimide compound solution 11 was prepared to have a concentration of 1% by weight with 50 mM borate buffer (pH 8.5). This solution was dispensed (0.5 ml), and its temperature was kept at 37° C. After that, 20 μg/ml of an M13 mp18ss solution (0.5 ml) was added, followed by shaking at 37° C. for 2 hours. This solution was centrifuged under a condition of 18,000 rpm at 4° C. for 1 hour to remove a supernatant.

(2) Prehybridization

A precipitate was suspended in a prehybridization solution (5× SSC, 5× Denhardt's solution, 25 mM phosphate buffer (pH 6.6), 50% formamide, 0.5 mg/ml denatured salmon sperm DNA), followed by shaking at 42° C. for 1 hour. This solution was centrifuged under a condition of 18,000 rpm at 4° C. for 1 hour to remove a supernatant. A precipitate was suspended in 10 mM sodium phosphate buffer (pH 7.4) to provide a solution having a concentration of 0.5% by weight.

(3) Hybridization

A hybridization solution (5× SSC, 1× Denhardt's solution, 25 mM phosphate buffer (pH 6.6), 45% formamide, 0.2 mg/ml denatured salmon sperm DNA, 20 ng/ml M13 mp18 RF, 200 μl) was added to the latex solution (200 μl) prepared as described in the items (1) and (2), and mixed, followed by shaking at 42° C. for 2 hours. A control was provided by replacing 20 ng/ml of M13 mp18 RF in the hybridization solution with pBR322, and it was reacted in the same manner as described above.

(4) Measurement of change in absorbance caused by agglutination reaction

In order to investigate the change in absorbance of the solution at a wavelength of 550 nm, the absorbance was measured immediately after the start of the reaction and 2 hours after the start of the reaction. A result is shown in Table 9.

TABLE 9

| DNA | Amount of change in absorbance value ($A_{550}$) |
|---|---|
| M13 mp18ss | 0.36 |
| pBR322 | 0.001 |

EXAMPLE 10

Detection of Human Plasminogen Based on Agglutination Method by Using Emulsive Carbo-Coated Latex (1) Immobilization of anti-human plasminogen antibody on carbo-coated latex A polystyrene latex comprising particles having a diameter of 0.15 μm coated with the carbodiimide compound solution 3 was prepared to have a concentration of 1% by weight with 50 mM borate buffer (pH 8.5). This solution was dispensed (1 ml), and its temperature was kept at 37° C. After that, anti-human plasminogen antibody (300 μg) was added, followed by shaking at 37° C. for 1 hour. This solution was centrifuged under a condition of 18,000 rpm at 4° C. for 1 hour to remove a supernatant.

(2) Blocking

A precipitate was suspended in a solution comprising 3% bovine serum albumin and 50 mM borate buffer (pH 8.5), followed by shaking at 37° C. for 1 hour. This solution was centrifuged under a condition of 18,000 rpm at 4° C. for 1 hour to remove a supernatant. A precipitate was suspended in 10 mM sodium phosphate buffer (pH 7.4) to give a solution having a concentration of 0.5% by weight.

(3) Measurement of change in absorbance by agglutination reaction

A human plasminogen solution (10 mg/ml, 50 μl) (3% bovine serum albumin, 10 mM sodium phosphate buffer (pH 7.4), 150 mM NaCl) and the latex solution (50 μl) with the immobilized anti-human plasminogen antibody prepared as described in the items (1) and (2) were added to 10 mM sodium phosphate buffer (pH 7.4) containing 150 mM NaCl (400 μl) and mixed. The change in absorbance of this solution at a wavelength of 660 nm was measured for 30 to 120 seconds after the start of the reaction. A test was performed as a control in the same manner as described above for 10 mg/ml of a human transferrin solution (3% bovine serum albumin, 10 mM sodium phosphate buffer (pH 7.4), 150 mM NaCl). A result is shown in Table 10.

TABLE 10

| | Amount of change in absorbance value ($A_{660}$) |
|---|---|
| plasminogen | 0.62 |
| transferrin | 0.005 |

EXAMPLE 11

Detection of DNA Based on Agglutination Method by Using Emulsive Carbo-Coated Latex (1) Immobilization of M13 mp18ss on carbo-coated latex A polystyrene latex comprising particles having a diameter of 0.15 μm coated with the carbodiimide compound solution 3 was prepared to have a concentration of 2% by weight with 50 mM borate buffer (pH 8.5). This solution was dispensed (0.5 ml), and its temperature was kept at 37° C. After that, 20 μg/ml of an M13 mp18ss solution (0.5 ml) was added, followed by shaking at 37° C. for 2 hours. This solution was centrifuged under a condition of 18,000 rpm at 4° C. for 1 hour to remove a supernatant.

(2) Prehybridization

A precipitate was suspended in a prehybridization solution (5× SSC, 5× Denhardt's solution, 25 mM phosphate buffer (pH 6.6), 50% formamide, 0.5 mg/ml denatured salmon sperm DNA), followed by shaking at 42° C. for 1 hour. This solution was centrifuged under a condition of 18,000 rpm at 4° C. for 1 hour to remove a supernatant. A precipitate was suspended in 10 mM sodium phosphate buffer (pH 7.4) to provide a solution having a concentration of 0.5% by weight.

(3) Hybridization

A hybridization solution (5× SSC, 1× Denhardt's solution, 25 mM phosphate buffer (pH 6.6), 45% formamide, 0.2 mg/ml denatured salmon sperm DNA, 20 ng/ml M13 mp18 RF, 200 μl) was added to the latex solution (200 μl) prepared as described in the items (1) and (2), and mixed, followed by shaking at 42° C. for 2 hours. A control was provided by replacing 20 ng/ml of M13 mp18 RF in the hybridization solution with pBR322, and it was reacted in the same manner as described above.

(4) Measurement of change in absorbance caused by agglutination reaction

In order to investigate the change in absorbance of the solution at a wavelength of 550 nm, the absorbance was measured immediately after the start of the reaction and 2 hours after the start of the reaction. A result is shown in Table 11.

TABLE 11

| DNA | Amount of change in absorbance value ($A_{550}$) |
|---|---|
| M13 mp18ss | 0.33 |
| PBR322 | 0.001 |

EXAMPLE 12

ELISA Detection of Oligopeptide Immobilized on Carbo-Coated PET Film (1) Immobilization of human ACTH on carbo-coated PET film Three dots of a human ACTH solution (10 mM HEPES (pH 7.0) were spotted onto a PET film coated with any of the carbodiimide compound solutions 1-4, 6, and 10-13 and onto a PET film not coated with the carbodiimide compound solution respectively, followed by immobilization at room temperature for 10 minutes.

(2) Detection of human ACTH by means of antigen-antibody reaction (a) Blocking

Blocking was performed at 25° C. for 30 minutes in a blocking solution (3% gelatin, 20 mM Tris-HCl buffer (pH 7.5) 0.5M NaCl).

(b) Antigen-antibody reaction

Incubation was performed at 37° C. for 2 hours in a solution of alkaline phosphatase-labeled anti-ACTH goat IgG (1% gelatin, 20 mM Tris-HCl buffer (pH 7.5), 0.5M NaCl, 0.05% Tween 20). Unreacted antibody was removed by washing with the washing solution 1 three times for 10 minutes in each washing, followed by replacement with the washing solution 2 (20 mM Tris-HCl buffer (pH 7.5), 0.5M NaCl).

(c) Color development operation

A solution of BCIP (50 mg 5-bromo-4-chloro-3-indolylphosphate, 900 ml dimethylformamide, 3.2 μl) was mixed with a solution of NTB (50 mg nitroblue tetrazolium, 1.8 ml 70% ethanol, 6.4 μl) to obtain a solution which was added to a buffer for substrate (0.1M Tris-HCl buffer (pH 9.5), 0.1M NaCl, 50 mM $MgCl_2$, 1 ml), followed by color development at room temperature for 3 hours. A result is shown in Table 12.

TABLE 12

| Carbodiimide solution | Result of color development |
|---|---|
| none | − |
| 1 | + |
| 2 | + |
| 3 | + |
| 4 | + |
| 6 | + |
| 10 | + |
| 11 | + |
| 12 | + |
| 13 | + |

+: color development, −: no color development.

What is claimed is:

1. A method for analyzing biologically active substances, comprising the steps of:

reacting a biologically active first substance immobilized on a carrier with a second substance capable of specifically binding the first substance; and detecting a non-bound second substance or a bound second substance so that the first substance or the second substance in a sample is analyzed;

wherein said carrier is adhered to a solid-phase base material, and comprises a compound, said compound comprising at least one polymer molecule, said polymer molecule having a molecular weight of not less than 1,000 and not more than 100,000, and having 2 to 100 carbodiimide groups thereon, and said first substance is immobilized to said carrier by covalently bonding to the carbodiimide groups.

2. A method according to claim 1, wherein a third substance capable of specifically binding the second substance is reacted after the first substance is reacted with the second substance.

3. A method according to claim 2, wherein said third substance is labeled with a label substance.

4. A method according to claim 3, wherein said label substance is selected from the group consisting of radioactive substance, fluorescent substance, enzyme, dye, chemical luminescent substance, biotin, avidin, streptoavidin, and digoxigenin.

5. A method according to claim 1, wherein said first substance is a first nucleic acid, and said second substance is a second nucleic acid having a nucleotide sequence substantially complementary to a nucleotide sequence of the first nucleic acid.

6. A method according to claim 1, wherein said carrier is emulsive.

7. A method according to claim 1, wherein said second substance is labeled with a label substance and said steps are comprised of:

reacting the first substance with the labeled second substance, detecting a non-bound labeled second substance or a bound labeled second substance indirectly bound to the carrier through binding between the first and second substances so that the first substance in a sample is analyzed.

8. A method according to claim 7, wherein said label substance is selected from the group consisting of radioactive substance, fluorescent substance, enzyme, dye, chemical luminescent substance, biotin, avidin, streptoavidin, and digoxigenin.

9. A method according to claim 1, wherein said second substance is unlabeled and said steps are comprised of:

adding a labeled substance, obtained by labeling the same substance as the unlabeled second substance with a label substance, to a reaction system of the first substance with the unlabeled second substance, competitively reacting the first substance with the unlabeled second substance and the labeled substance, detecting the labeled substance indirectly bound to the carrier through binding between the first substance and the labeled substance so that the second substance in a sample is analyzed.

10. A method according to claim 9, wherein said label substance is selected from the group consisting of radioactive substance, fluorescent substance, enzyme, dye, chemical luminescent substance, biotin, avidin, streptoavidin, and digoxigenin.

11. A method according to claim 1, wherein said first substance is a first protein, peptide, or another antibody-binding substance, and said second substance is a second protein, peptide, or another antibody-binding substance capable of specifically binding the first protein, peptide, or another antibody-binding substance.

\* \* \* \* \*